(12) United States Patent
Morgan

(10) Patent No.: US 7,214,062 B2
(45) Date of Patent: May 8, 2007

(54) METHOD AND APPARATUS FOR REPLICATING THE POSITION OF INTRA-OSSEOUS IMPLANTS AND ABUTMENTS RELATIVE TO ANALOGS THEREOF

(75) Inventor: Vincent J. Morgan, Boston, MA (US)

(73) Assignee: Debbie, LLC, Boston, MA (US)

( * ) Notice: Subject to any disclaimer, the term of this patent is extended or adjusted under 35 U.S.C. 154(b) by 507 days.

(21) Appl. No.: 10/732,526

(22) Filed: Dec. 11, 2003

(65) Prior Publication Data

US 2004/0121287 A1     Jun. 24, 2004

(51) Int. Cl.
*A61C 8/00* (2006.01)

(52) U.S. Cl. ...................................................... 433/173

(58) Field of Classification Search ................ 433/172, 433/173, 174, 175
See application file for complete search history.

(56) References Cited

U.S. PATENT DOCUMENTS

| 4,738,623 A | | 4/1988 | Driskell | |
| 5,658,147 A | * | 8/1997 | Phimmasone | ................ 433/213 |
| 5,810,590 A | * | 9/1998 | Fried et al. | .................. 433/172 |
| 6,382,977 B1 | * | 5/2002 | Kumar | ........................ 433/214 |

* cited by examiner

*Primary Examiner*—Melba Bumgarner
(74) *Attorney, Agent, or Firm*—John A. Haug

(57) ABSTRACT

The position of intra-osseous implants and abutments to analogs is enabled and enhanced by using the longitudinal axial locked position of a post (12*a*) of an implant (12) having a locking taper in a bore (10*a*) of an implant (10) having a generally matching locking taper as a reference to determine the position of a stop surface (14*c*) on impression posts, abutment analog posts and the like received in the bore of an implant and implant analog. In another embodiment the bore (16) of an implant analog (16) is provided with a shelf (16*c*) located at a position determined by the axial distance of the locked position of the abutment post to prevent over-seating. Controlled retentive resistance and stability of a post is provided by using flats formed in the bore of an implant analog and by forming rings on a post receivable in the bore of an implant or implant analog. One such ring (18*c*) is formed with an outer periphery sized and configured to allow bending of the outer peripheral portion in a direction opposite to the direction of insertion in a bore to provide greater retentive resistance than insertion resistance.

5 Claims, 4 Drawing Sheets

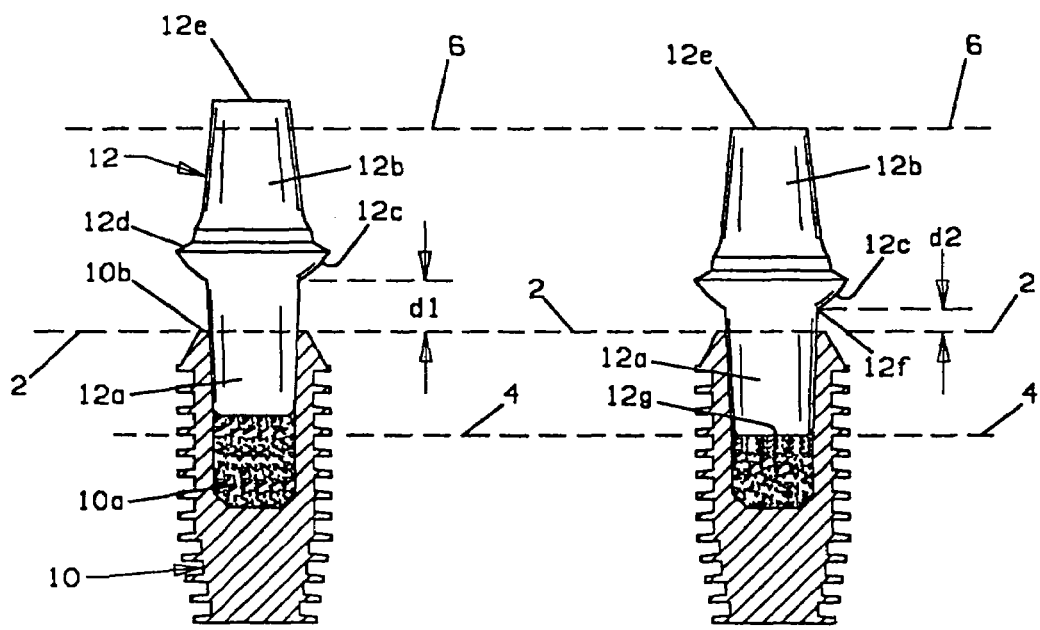
FIG 1a
PRIOR ART
FIG 1b
PRIOR ART
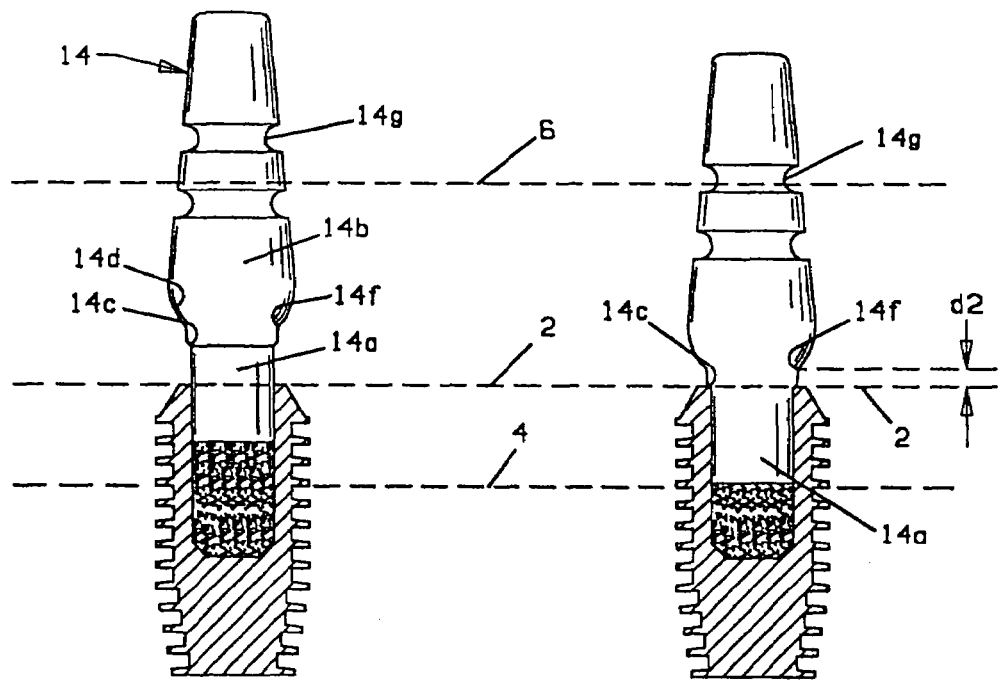
FIG 1c
FIG 1d

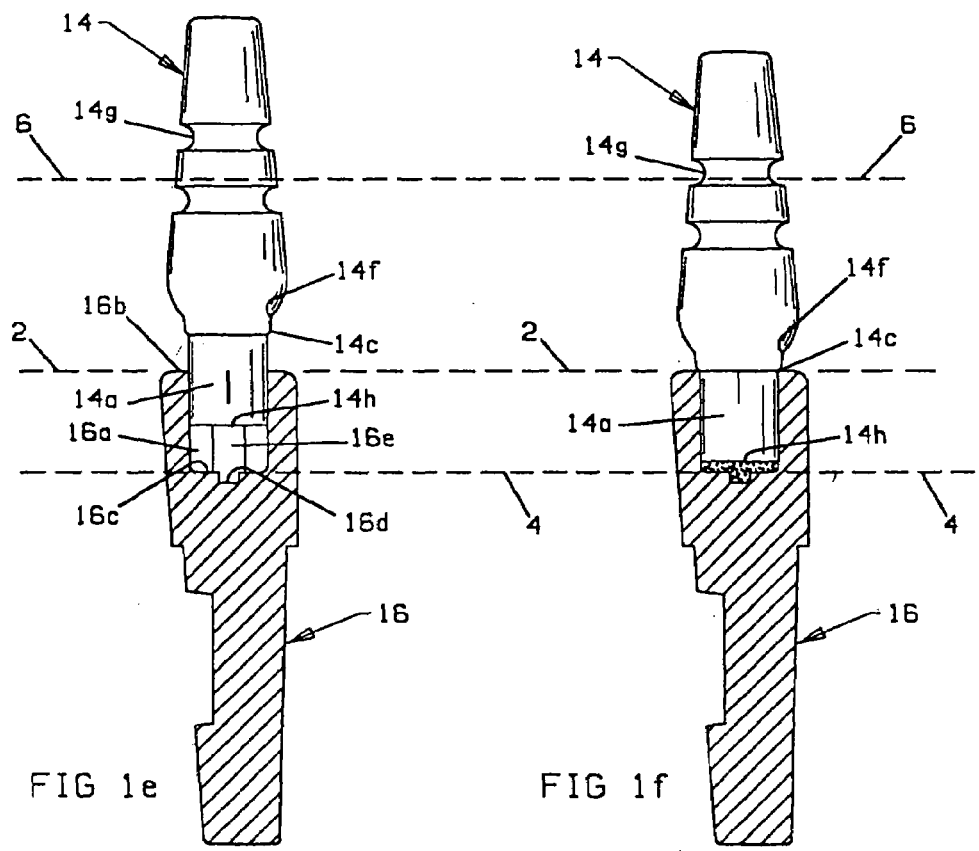
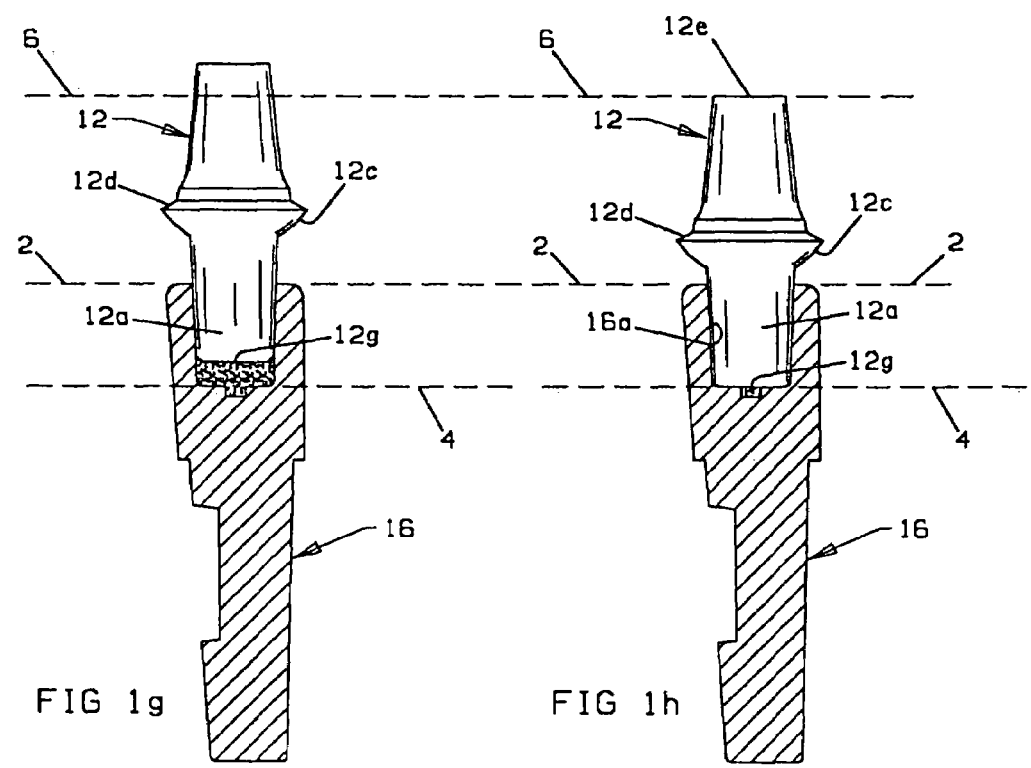

US 7,214,062 B2

METHOD AND APPARATUS FOR REPLICATING THE POSITION OF INTRA-OSSEOUS IMPLANTS AND ABUTMENTS RELATIVE TO ANALOGS THEREOF

RELATED APPLICATIONS

Benefit is claimed of provisional application No. 60/274,498 filed Mar. 9, 2001.

FIELD OF THE INVENTION

This invention relates generally to medical and dental implant devices and more particularly to a method for transferring the relative position of an intra-osseous implant relative to a laboratory replicated position, as in a dental abutment, and for determining the appropriate height of a dental abutment received in an implant for an aesthetic submucosal prosthetic margin placement.

BACKGROUND OF THE INVENTION

Implant systems comprising an implant having a tapered bore adapted to receive therein an abutment post or the like formed with a matching taper for retention of the post in the implant are known. See for example U.S. Pat. No. 4,738,623, assigned to the assignee of the present invention, the disclosure of which is incorporated herein by this reference. It is also known to provide such posts, which are intended to be used as impression posts or temporary abutment posts, with a longitudinally extending slot in the end thereof in order to more easily remove the posts. Generally, such posts are made of titanium or titanium alloy due to their biocompatibility characteristics. However, titanium has a major limitation relating to the phenomenon of memory. It is possible for the diameter of the slotted post to either widen or narrow over time making the nature of the fit of the post in an abutment unpredictable. The property of memory can cause an abutment to become loose in clinical function and result in an unpredictable degree of retention.

There is a need to be able to replicate the position that an abutment would have in an implant in a system using abutment analogs, impression posts and the like made of the same or different materials which accurately and reliably correspond to the locked position of a permanent abutment in an intra-osseous implant. Among the factors which need to be dealt with in doing this is the existence of hydraulic pressure resisting the seating of a post as well as the need for having the post retain its seated position whether gravity is adding a force against seating or toward seating, as in the use in upper teeth versus lower teeth. There is also a need to be able to determine the appropriate height of an abutment which will provide an aesthetic submucosal prosthetic margin placement.

SUMMARY OF THE INVENTION

It is an object of the invention to overcome the prior art limitations noted above. Another object of the invention is the provision of an impression post and any other post, such as a temporary abutment post, wherein a clinician will want to remove the post with minimal, predictable effort.

Briefly, in accordance with one embodiment of the invention, the post of a member, such as an abutment analog, impression post, implant transport handler, healing plug and the like, is formed with a radially outwardly extending stop surface such as a shelf having a diameter larger than the diameter of the bore in a permanent implant and an implant analog and located at a distance from the longitudinal axial position of a reference location of a head formed on the post essentially equal to the distance from the top end surface of a permanent implant to a corresponding reference location of a head of an abutment with the abutment in a clinically locked position as a result of being tapped into the implant.

According to another embodiment, an implant analog is formed with a shelf in the bore of the implant analog located at a distance from the mouth of the bore, i.e., the top surface of the implant analog, essentially equal to the distance between the bottom end face of the tapered post of a permanent abutment and the longitudinal axial position on the tapered post at the top face surface of the permanent implant with the permanent abutment in the locked position upon receiving clinical tapping insertion force. The shelf prevents a tapered permanent abutment post from overseating in an implant analog, which is particularly important when the implant analog is composed of plastic material. According to a feature of the invention, the cylindrical bore of the implant analog can be provided with one or more flats to increase the retention resistance of a cylindrical post, with or without a taper, received therein as well as to provide an axially extending air passage to relieve or prevent the build up of hydraulic pressure in the closed end of the bore.

According to a feature of the invention, retentive resistance of the post of the abutment analog, impression post, implant transport handler, healing plug and the like can be increased by forming one or more circumferential rings about the posts, at least one of the rings having an outer diameter larger than the diameter of an implant bore to form an interference fit and preferably, the at least one ring being flexible and having a feathered, or otherwise shaped configuration so that upon being inserted into the bore of the implant the outer peripheral portion of that ring will bend in a direction opposite to the direction of insertion so that upon removal of the post the outer peripheral portion of the ring will have to bend back on itself thereby requiring a greater removal force than insertion force.

According to yet another embodiment of the invention, an elongated probe member having a size to be freely insertable in the bore of an implant is formed with a plurality of axially positioned index configurations, such as circumferential grooves, located in the probe member at selected distances from the free distal end of the probe member corresponding to the position of given reference locations of a clinically seated abutment in the implant. The index configurations indicate the axial position of a given geometry of the implant bore as a reference point so that the appropriate height of an abutment shoulder can be determined to achieve an aesthetic submucosal prosthetic margin placement.

Additional objects and features of the invention will be set forth in part in the description which follows and in part will be obvious from the description and drawings. The objects and advantages of the invention may be realized and attained by means of the instrumentalities, combinations and methods particularly pointed out in the appended claims.

BRIEF DESCRIPTION OF THE DRAWINGS

The accompanying drawings, which are incorporated in and constitute a part of the specification, illustrate preferred embodiments of the invention and, together with the description, serve to explain the objects, advantages and principles of the invention. In the drawings:

FIGS. 1a, 1b are cross sectional views which show a prior art arrangement of an abutment received in the bore of an implant using a first level of pressure, such as finger pressure and a second level of pressure, such as by clinically applied tapping, to a locked position in the bore, respectively; FIGS. 1c, 1d are similar cross sectional views which show an impression post made in accordance with a first embodiment of the invention, partially received in the bore of an implant and fully seated therein, respectively; FIGS. 1e, 1f are similar cross sectional views which show an impression post partially received in the bore of an implant analog made in accordance with another embodiment of the invention and fully seated therein; and FIGS. 1g, 1h are similar cross sectional views which show an abutment partially received in the bore of the implant analog of FIGS. 1e, 1f and fully seated therein, respectively;

DETAILED DESCRIPTION OF THE PREFERRED EMBODIMENT

Figure 2:
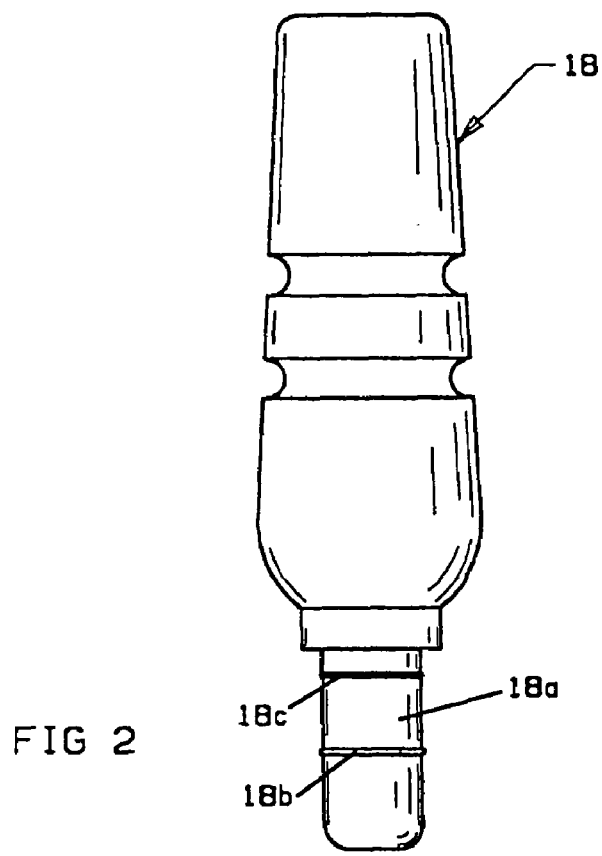
FIG. 2 is an elevational view of an impression post made in accordance with another embodiment of the invention and FIG. 2a is an enlarged, broken away portion of FIG. 2.

With reference to FIGS. 1a, 1b, a conventional implant 10 is shown having a well or bore 10a formed with a female locking taper as disclosed in detail in U.S. Pat. No. 4,738,623 referenced above. Dashed line 2 extends through the top end surface 10b of the implant shown in FIGS. 1a–1d and the top end surface 16b of the implant analogs shown in FIGS. 1e–1h to be discussed. Dashed lines 4 and 6 show the same reference distances from dashed line 2 in the respective figures. The post 12a of an abutment 12, also provided with a male locking taper, is received in bore 10a at a first apical position relative to the top end surface 10b of the implant when a first lower pressure level is used to place the implant, as by finger pressure. Dashed line 2 aligned with the top end surface 10b denotes the axial position of post 12a in the first, partially seated position at a distance d1 measured along the longitudinal axis of post 12a and bore 10a from a reference point of the abutment, e.g., the lower end of basal portion 12c of head 12b. Abutment 12 is shown with a head 12b including curved basal portion 12c and shoulder 12d for receiving thereon a suitable crown or the like, not shown. FIG. 1b includes the same implant and abutment but is shown with the abutment post after being seated in a second locked position as by tapping the abutment with a clinically applied tapping force. In the fully seated second position the axially measured distance between dashed line 2 and the same reference point is d2. The change in the apical positions of FIGS. 1a and 1b has been shown to be 0.006 inch for 0.0785 inch diameter post and 0.010 inch for 0.1185 inch diameter post systems having a locking taper of 1.5 degrees and received in respective bores of 0.0785 inch and 0.1185 inch having a matching locking taper. The distance d2 is the average distance which was determined by taking a group of abutments for each diameter post and measuring the individual d2 distance for each abutment upon clinical seating thereof. The distance is essentially equal from one abutment to another of a group within manufacturing tolerances and with little or no difference noted for any variations of clinical insertion force used.

In accordance with a preferred embodiment of the invention, a radial, outwardly extending shoulder 14c is formed on post 14a of impression post 14 at an axial distance d2 from a reference point 14f corresponding to the reference point 12f of the abutment shown in FIGS. 1a, 1b. The outer portion of post 14a is preferably formed with no taper and with a diameter to permit full insertion into the tapered bore of implant 10. The provision of shoulder 14c, chosen to have an outer diameter greater than the opening of bore 10a, results in placement of head portion 14b in essentially the same position in implant 10 as head 12b of abutment 12 in implant 10. A reference configuration, e.g., circumferential groove 14g of post 14 can be used to reflect the position of top end face 12e of an abutment as noted by dashed line 6. Although an impression post member is shown in the drawings, it will be understood that shoulder 14c can be provided on the post of other members such as abutment analogs, healing plugs and the like for receipt in the bore of an implant to obtain the same benefits. Further, it should be realized that shoulder 14c can be discontinuous or formed as spaced apart stop surfaces, if desired.

Referring to FIGS. 1e–1h, an implant analog 16 made in accordance with another embodiment of the invention comprises a body made of polycarbonate or other suitable plastic such as ultra high molecular weight polyethylene (UHMW-PE), or a composite, ceramic or metal and is shown having a bore 16a of generally the same diameter as bore 10a of implant 10 however the bore may have a straight bore if desired. Bore 16a is formed with a shelf 16c formed at a depth or axial distance from the end face surface 16b of the implant analog which is essentially the same as the distance between dashed lines 2 and 4, that is, the axial distance from the top end surface 10b of implant 10 and the bottom end face surface 12g of abutment 12 when in the second, fully seated locked position of FIG. 1b. Placement of shelf 16c in this position limits travel of an abutment post when inserted into bore 16a as shown in FIG. 1h and prevents over-seating of an abutment having no shoulder on the post thereof for that purpose. Bore 16a preferably extends beyond shelf 16 as indicated at 16d to minimize the effects of hydraulic pressure build up as a post is inserted in the bore. Preferably the axial distance of post 14a of impression post 14 from shoulder 14c to end face surface 14h of the post is selected to be slightly less than the distance of post 12a of abutment 12 from an axial location at dashed line 2 in FIG. 1b indicating a clinically seated abutment and end face surface 12g of the abutment to ensure that shoulder 14c limits travel as it engages top end surface 16b of implant analog 16.

Typically, implants 10 and abutments 12 are composed of titanium or titanium alloys for biocompatibility while the implant analogs and impression posts and the like are composed of plastic such as polycarbonate and ultra high molecular weight polyethylene (UHMW-PE), composites or other suitable materials. This results in a problem in simulating the locking taper of the titanium implants and abutments when using a different material for the abutment analog or impression post and when using them without a locking taper. That is, the problem of achieving the same axial displacement without the same retention and in achieving the same lateral stability of the posts from one female bore to another. According to a modified embodiment of the invention, one or more flat surfaces 16e (FIG. 1e) is formed in bore 16a of implant analog 16 to form a limited interference with a generally cylindrical post to increase retentive force and stability of a post received therein. Usually, a plurality of flats, preferably symmetrically spaced about the periphery of the bore, are formed to provide consistent placement of a post in the bore of an implant analog relative to the bore of an implant. Such flats also provide an axially extending air passage to allow air to escape as a post is being inserted in the bore and thereby minimize hydraulic pressure build up.

Figure 2A:
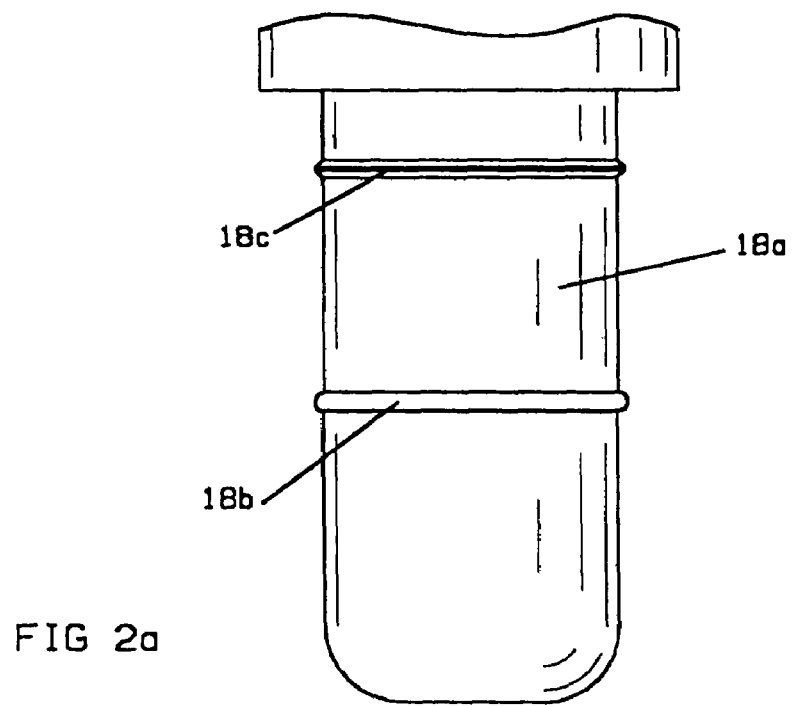

FIGS. 2 and 2a show an impression post 18 made in accordance with another preferred embodiment of the invention which is formed of suitable material which in thin configurations has a degree of flexibility, such as some plastic materials, e.g., polycarbonate or ultra high molecular weight polyethylene (UHMW-PE), and formed with circumferentially extending rings or rib like formations 18b, 18c on the portion of post 18a receivable in the bore of an implant or implant analog. Post 18a is cylindrical and can be formed with or without a taper. At least one of the rings is formed to provide an interference fit. Ring 18b is used in cooperation with ring 18c to provide enhanced lateral stability in a bore. Ring 18c has a slightly larger diameter than ring 18b to form an interference fit and is somewhat feathered at its outer periphery or otherwise configured to allow it to be bent in a direction toward or away from the distal free end of the post. When used in a properly sized bore with or without a locking taper, the material of ring 18c is bent upon insertion of the post into such a bore in a direction opposite to the direction of insertion with the outer portion of the ring material being closer to the entrance to the bore than the remainder of the ring. When the post is then removed the outer portion bends back in the opposite direction, that is, in effect, it is folded back on itself into an ogee type of configuration, due to the limited space available, with the base of the ring or rib like formation gradually advancing to the position of the outer portions and finally assuming a position with the base portion being closer to the entrance of to the bore than the outer portion. This reverse bending increases the retentive force required for removal, in a manner predictably controlled by the material and dimensions of the rings relative to the bore. As a result of this, the force required to remove the post from such a bore is greater than the force required to insert the post into the bore. It will be understood that ring 18c can be used by itself, if desired, to provide a retention resistance greater than an insertion resistance for a post. Likewise, ring 18b can be used by itself to provide lateral stability as well as retention resistance with the ring having a tight fit or an interference fit, as desired. It will also be understood that rings as described above can be provided on the posts of other members receivable in the well of an implant abutment, e.g., an abutment analog.

Impression posts were made in accordance with the invention having a nominal post diameter of $0.113/0.112$ inch for a 0.1185 inch diameter bore and provided with first and second spaced apart, circumferentially extending, rings or rib like formations. The first ring, closest to the free end of the post has an outer diameter of $0.116/0.115$ inch and the second ring has an outer diameter of $0.119/0.118$ inch. Members having another post size were made having a nominal post diameter of $0.073/0.072$ inch for a 0.0785 inch diameter bore, the first ring has a diameter of $0.076/0.077$ inch and the second ring has a diameter of $0.079/0.080$.

Figure 3A:
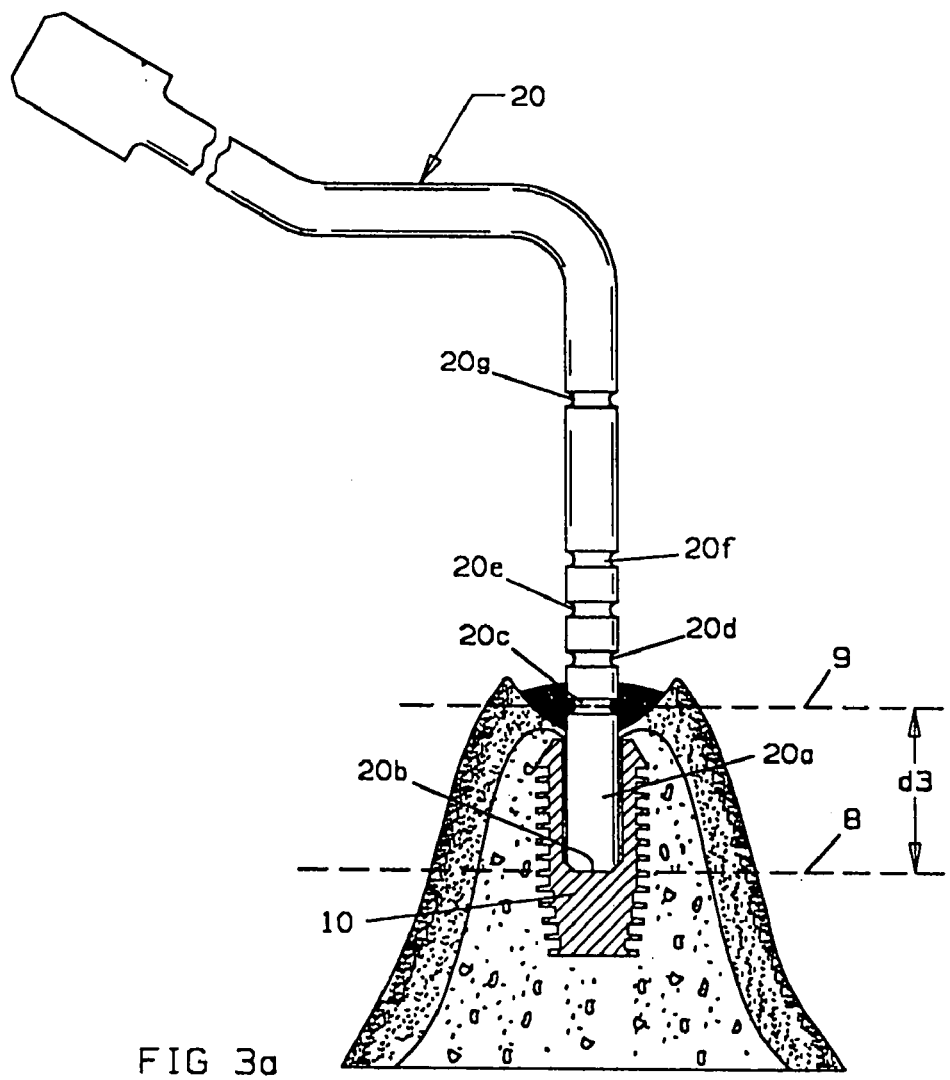
FIG. 3a is a cross section view taken through an intra-osseous mounted implant with an indicator probe made in accordance with the invention received in the bore of the implant.
Figure 3B:
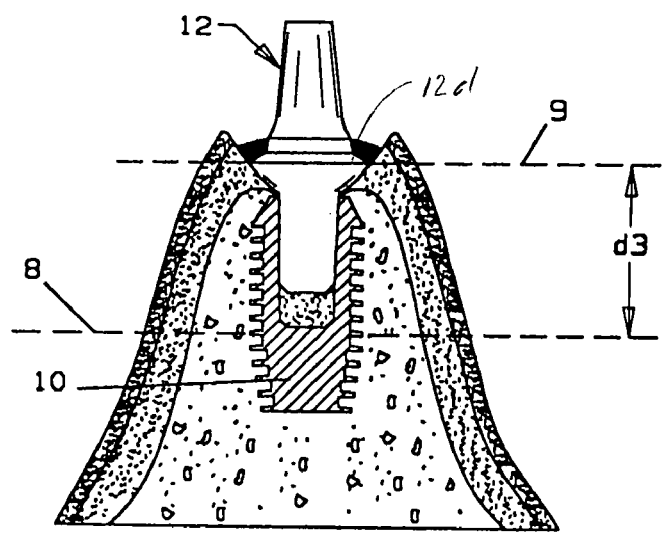
FIG. 3b is a view similar to FIG. 3a but showing an abutment received in the bore of the implant at an apical position related to index configurations of the indicator probe.

With reference to FIGS. 3a and 3b, a generally elongated indicator probe 20 comprises a head portion 20a formed with an outer periphery of a size selected to be freely received in the bore of an implant 10 with the distal free end engaging the bottom wall of the bore. Implant 10 is shown in the drawings implanted in the bone of a patient. Horizontally extending, spaced apart index points or configurations 20c are formed on the probe body at locations corresponding to the axial positions of reference points or configurations of an abutment 12 (FIG. 3b) to be clinically seated in the implant. For example, a longitudinal axial distance d3 from the bottom surface of the bore of implant 10, represented by dashed line 8, to shoulder 12d of abutment 12, represented by dashed line 9, clinically seated in the second locked position in the implant as shown and described in FIG. 1b, is essentially the same as the axial longitudinal distance d3 from the distal end surface 20b to index configuration 20c of probe 20 when bottomed out in the bore of implant 10 of FIG. 3a. Thus probe 20, when seated in the bore of an intra-osseous implant will indicate the axial position of various geometries on posts inserted into the implant relative to the height of soft tissues overlying the implant by index configurations 20c–20g.

Axial adjustment is essential for the fabrication of integrated abutment crowns, i.e., prefabricated or custom crowns mounted, bonded or fabricated on abutments extra-orally, where the proper anatomical relationships and adjustments needed to obtain them are greatly enhanced and facilitated by means of the above described features of the invention.

Although the invention has been described with regard to a certain specific embodiment thereof, variations and modifications will become apparent to those skilled in the art. For example, although the post is described as generally cylindrical, it is within the skill of the art to use any selected outer configuration, such as elliptical, if desired, in conjunction with rib like formations extending around the circumference as taught by the invention. It is, therefore, the intention that the appended claims be interpreted as broadly as possible in view of the prior art to include all such variations and modifications.

What is claimed:

1. The method of replicating the relative position of an abutment locked to an implant to an abutment analog received on an implant analog, the abutment having an abutment post formed with a locking taper receivable in a bore of the implant formed through a top surface of the implant, the implant bore formed with a matching locking taper, the abutment post received at a first axial position in the implant bore upon use of a first relatively low insertion force and a second fully locked axial position upon use of a second relatively higher insertion force, the implant bore extending beyond the post of the abutment in the second locked axial position, the abutment analog having an abutment analog post receivable in a bore of the implant analog comprising the method steps of selecting a first reference location on the abutment and a corresponding first reference location on the abutment analog, determining a longitudinal distance d between the first reference location of the abutment and the top surface of the implant when in the second locked axial position, taking an implant analog having a top end surface, forming a longitudinally extending bore through the top end surface of the implant analog extending into the implant analog to a stop surface at a depth selected to limit insertion of the abutment analog to a position at which the corresponding first reference location of the abutment analog is at the longitudinal distance (d) from the top end surface of the implant analog, determining an axial distance from the top surface of the implant to a second reference location of the abutment when in the second locked axial position as a replication distance, forming an index configuration on the abutment analog at the replication distance along the longitudinal axis from the top end surface of the implant analog when the abutment analog is fully inserted in the implant analog with the abutment analog post engaging the stop surface, and inserting the post of the abutment analog into the bore of the implant analog until movement of the post of the abutment analog is limited by the stop surface to obtain a replicated position of the second reference location of the abutment in the second locked position as reflected by an axial position of the index configuration of the abutment analog.

2. The method of claim 1 further comprising the step of mitigating the build-up of fluid pressure in the bore of the implant analog incident to the insertion of a post into the implant analog bore.

3. The method of claim 2 in which the build-up of fluid pressure is mitigated by forming at least one flat surface in a circumference of the bore of the implant analog so that there is line contact between the abutment analog post and the flat surface thereby leaving an opening on either side of the line contact.

4. The method of claim 2 in which the build-up of fluid pressure is mitigated by extending the depth of only a portion of the implant analog bore beyond the stop surface.

5. The method of claim 1 in which the second reference location of the abutment is an outermost surface of the abutment.

* * * * *